United States Patent [19]

Ishida et al.

[11] 4,213,857

[45] Jul. 22, 1980

[54] ANAEROBIC DIGESTION PROCESS

[75] Inventors: Masahiko Ishida; Ryoichi Haga; Yoji Odawara, all of Hitachi, Japan

[73] Assignee: The Agency of Industrial Science and Technology, Tokyo, Japan

[21] Appl. No.: 942,285

[22] Filed: Sep. 14, 1978

[30] Foreign Application Priority Data

Sep. 14, 1977 [JP] Japan .................... 52-109973

[51] Int. Cl.² ................................ C02C 1/16
[52] U.S. Cl. ......................... 210/6; 210/8; 210/12; 210/16
[58] Field of Search ............................ 210/2-8, 210/12, 16, 18, 180, 197, 218, 10, 15, 195.3, 195.1

[56] References Cited

U.S. PATENT DOCUMENTS

| 3,622,507 | 11/1971 | Pasveer | 210/6 |
| 3,649,534 | 3/1972 | Schotte | 210/10 |
| 3,772,191 | 11/1973 | Thorn | 210/10 |
| 3,981,800 | 9/1976 | Ort | 210/16 |
| 4,134,830 | 1/1979 | Skogman et al. | 210/16 |

OTHER PUBLICATIONS

Ghosh S. et al., "Anaerobic Acidogenesis of Wastewater Sludge", Journal W.P.C.F., vol. 47, No. 1, Jan. 1975, pp. 30-45.

Primary Examiner—Benoit Castel
Attorney, Agent, or Firm—Birch, Stewart, Kolasch and Birch

[57] ABSTRACT

The present invention relates to a process for digestion treatment of organic wastes that are difficult to digest, with a high efficiency and an improved recovery rate of methane.

The wastes, before subjected to anaerobic treatment, are heated at 55°–75° C. within an acid or alkaline solution for dissolving digestible ingredients and the insoluble ingredients are eliminated before being transferred to an anaerobic digestion step. By exercising a pre-treatment for dissolving and separating digestible ingredients, the size of the container will be minimized as a result of the shortened time required for digestion and the recovery rate of methane will be improved.

21 Claims, 2 Drawing Figures

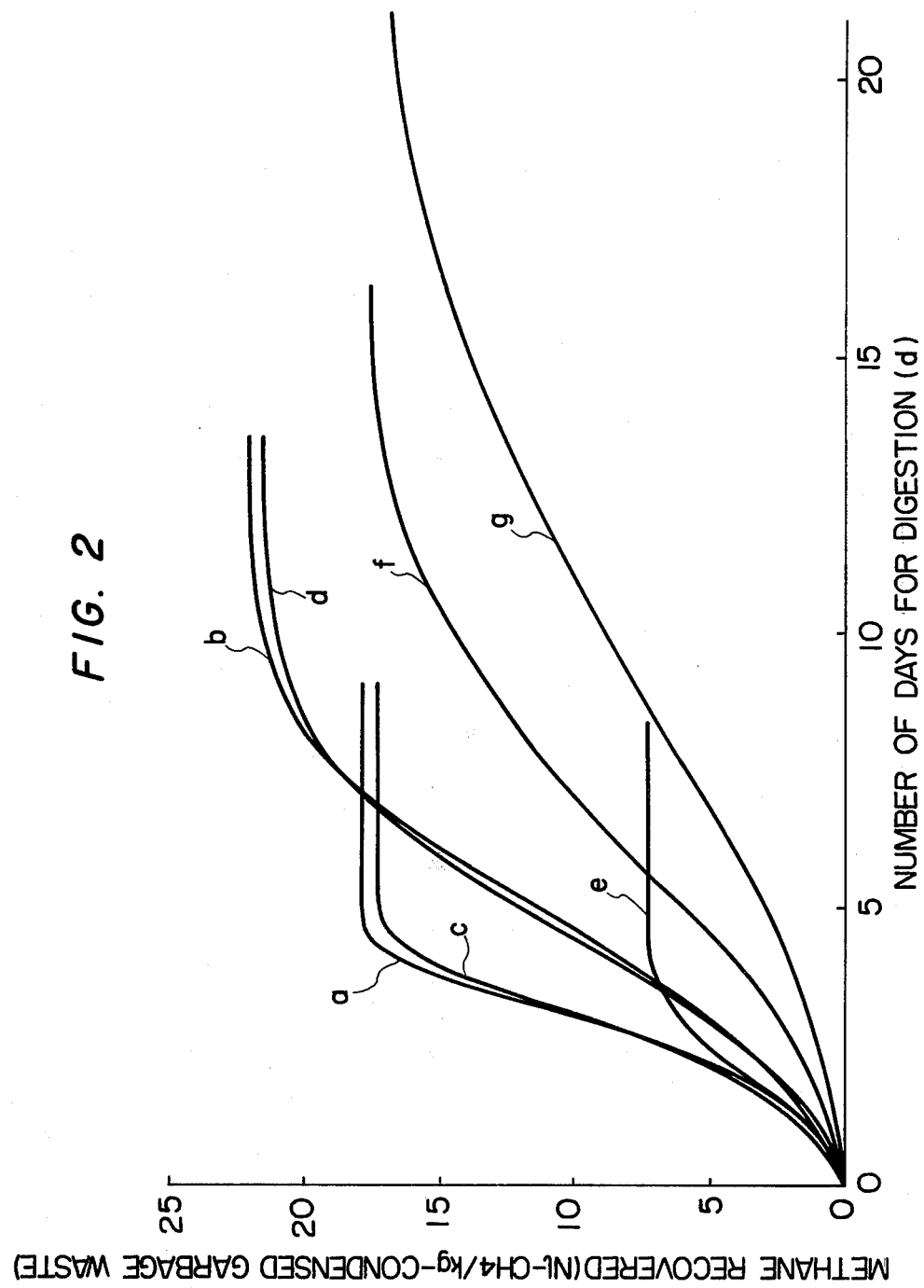

ANAEROBIC DIGESTION PROCESS

BACKGROUND OF THE INVENTION

Present invention relates to an anaerobic digestive process which is suitable for a quick treatment of organic wastes, particularly those containing much solids.

Presently most of such organic wastes as excess activated sludge which is by-produced at the time of sewage treatment, agricultural and livestock waste and city garbage are being incinerated or landfilled or dumped. Among others, those wastes which contain much solids are not easy to dispose, and in many instances they are causing such problems a pollution by stack smoke, stench, water contamination, soil contamination and so forth.

Recently, general attention is being focused upon the anaerobic digestive process, as a non-polluting and energy-saving process which will replace the aforementioned procedures. This process has conventionally been employed for treating the collected human wastes in Japan and for treating the sludge used for treating sewage wastes in other countries. However, it has the disadvantage that it requires a rather extended period of time, 20 to 40 days, to complete the digestion. Therefore, if the process could be made speedier, it would be a very useful process. On the other hand, even for anaerobic digestion, human and animal wastes, agricultural and livestock wastes as well as city garbage are the materials which are difficult to dispose. As practical examples, (1) Only a very limited part of cellulose, pectin and hard protein, which are the main ingredients of the solids, is decomposed, and the most of them remain intact within the digestive sludge without being decomposed before discharge out of the system. Of course, the same applies to city garbage which involves such variety of admixture as waste plastics, sand and dirt, and numerous pieces of glass. (2) These solids burden the transmission system of the charged slurry and the stirring system installed in the digestion tank, which results in problems in the treatment system. In particular, it encourages a generation of scum in the digestion tank and cause a deterioration in the mixing state of the liquor, so that the number of days required for digestion will have to be extended which prevents a satisfactory methane fermentation. Further, it causes more power consumption for stirring and requires additional labor for taking out the scum for disposal.

In the past situations of disposing of collected human wastes and in experiments for treating city garbage disposal, solids were anaerobically digested after being crushed into pieces having a certain particle size, but in either cases the aforementioned points were the problem. Although there is an example wherein the liquor only is subjected to the methane fermentation, removing in advance those undigestible solids, a decline in the methane yield is inevitable since only a 50% at maximum out of the total decomposable ingredients could be extracted by treating it with water after simply crushing and mixing them. In addition, it is not easy to dispose of the residue, due to an incomplete extraction of decomposable ingredients.

Previously, the present inventors had found an effective method of treating organic waste that can increase methane yield and can reduce the number of days required for fermentation. The features of this method are to ferment anaerobically organic waste after heating treatment of organic waste acidified by adding acid. (U.S. Application, Ser. No. 651,586: "Method and Apparatus for the Treatment of Waste", filed on Jan. 22, 1976, M. Ishida et al.) now abandoned.

They, also, had found a method that is in no way inferior to the above-mentioned method. The features of this method are to partially decompose the uneasily decomposable materials such as protein, liquid, etc. in organic waste by using alkali instead of the acid. (U.S. Application, Ser. No. 843,262: "Process for Anaerobic Digestion of Biochemical Waste", filed on Oct. 22, 1977, M. Ishida et al.) now abandoned.

SUMMARY OF THE INVENTION

The purpose of the present invention is to eliminate the aforementioned defects of the conventional technique and to make available an anaerobic digestive process with high efficiency and digestibility for treating organic wastes.

In summary, the characteristic features of present invention are, first, to effectively extract such decomposable ingredients as protein, starch, fat and low molecular weight substances by treating organic wastes in the presence of water at 55°–75° C. at below pH 2.5–4.0 or above pH 8.0–9.8 (hereafter abbreviated to decomposition treatment), and at the same time to lower the viscosity of slurry by a partial chemical decomposition of the first three of the above ingredients, whereby facilitating subsequent anaerobic digestion.

The second step is to separate the decomposed slurry into liquid and residue through a solid liquid and to subject the liquid alone to anaerobic digestion. Thereby, as mentioned in the above, such defects as scum generation within the digestive liquor due to the solids mixed in, troubles in transmission and stirring of slurry, higher power consumption for stirring, increased dimension of tanks and so forth, could be eliminated.

The third characteristic point is that the residue obtained through a solid liquid separation of the residue slurry after decomposition is washed by the treated water obtained by an aerobic treatment of the digested separate water, as will be described later. This will improve further the extraction rate of decomposable ingredients and the easiness in disposing of the residue, and further will serve to improve the purity of the product as a starting material for subsequent effective use of such products. It is only because of the fact that, by only separating the residue slurry after decomposition into solids and liquor, the decomposed residue is left in a humid state on account of the liquor which contains digestive substances, and not only has it a stench in itself but it easily becomes putrefied and emits an offensive odor.

The fourth characteristic is that the waste water used for washing the aforementioned residue can be re-used for making a slurry for decomposing the organic waste, thereby enabling the effective recuperation of the decomposable ingredients in the wash waste water and to reduce the total water consumption as well as the treated water to be discharged from the system.

BRIEF DESCRIPTION OF THE DRAWING

FIG. 2 shows the number of days required for digestion and the recovered volume of methane.

DESCRIPTION OF THE EMBODIMENT PREFERRED

Figure 1:
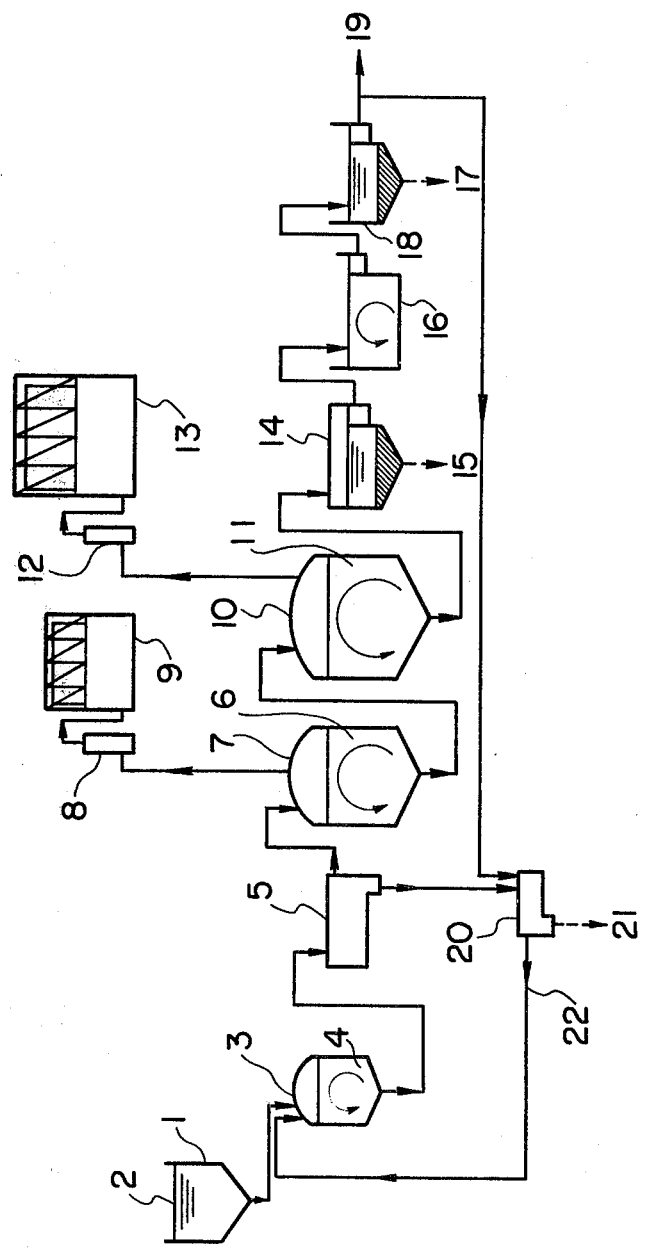
FIG. 1 illustrates an example of flow-sheet related to the present invention.

FIG. 1 shows one example of the process of the present invention, and an explanation in detail follows in the following paragraphs.

Organic waste 2, e.g. agricultural and livestock waste, human and animal waste, alcohol brewery waste water and city garbage, which are stored in organic waste storage tank 1, are to be charged into decomposition tank 3. In order to turn it into a slurry 4 at this point, the waste wash water is charged into the tank. This water waste wash discharges from washing the decomposed residue by aerobic treatment water 19 of the digested separate water, to which a reference will be made later, and makes it a slurry of dried solid concentration, below 20%. Next, the slurry is heated up to 55°–75° C. at a pH of 2.5–4.0 or above a pH of 8.0–9.8. Although the effective pH at the decomposition treatment is as mentioned above, a suitable pH, upon taking into account the economics, would be a pH of 2.5–4.0 or a pH of 8.0–9.8. As for an acid that will be used for acidification, other than such mineral acids as hydrochloric acid and sulphuric acid, such organic acids as acetic acid and citric acid, are also effective. Economically, however, hydrochloric acid and sulfuric acid are most suited, and the addition of a highly concentrated acid is far more convenient in view of its lesser dilution. In general, to attain the aforementioned effective pH, an the addition of a 35% HCl by 0.1–1% (wt/wt) is necessary. Besides the above, the alkali that will be used for alkalification includes calcium hydroxide, calcium oxide, and carbide residue from acetylene production. The treatment temperature may range from room temperature to 75° C., but the range of 55°–75° C. will be more practical. Treatment time will be 1–24 hours at 55° C. Next, the slurry which finished the aforementioned decomposition treatment is into a liquid phase separate and a residue by means of the solid liquid separator 5. As for the solid liquid separation method, conventional methods as pressure filtration, centrifugal separation, centrifugal filtration, vacuum filtration and sedimentation separation are fully capable of treatment. Provided, however, sedimentation separation will be used in case where the concentration of slurry is low, or as a preliminery treatment. Wherever possible, it is most desirable to make the water content of the residue below 80%.

The separated liquid part obtained as above will be transferred to the anaerobic digestion tank 7 and 10. As for the digestion method to be employed here, it would be either the conventional parallel-dual fermentation or liquified-gasified two-step treatment which permits a speedier operation. In case of the parallel-dual fermentation method, its operation is performed under an anaerobic condition at below 75° C. As exhibited by an example shown in the drawing attached, in case of the two-step treatment, first, the waste will be charged into the liquefaction tank 7 and let it contact with liquefaction bacteria, and will be kept stirred for one to several days under an anaerobic condition at a predetermined temperature below 75° C. At this liquefaction step, the organic substances chemically decomposed in part by decomposition treatment will be further turned into lower molecular weight substances, and eventually they will be decomposed into volatile fatty acid and carbon dioxide. Suitable pH is 4–7 and it could be opened depending on the nature of the waste water and the variety of the bacteria to be used. As the liquid becomes acidic in the course of liquefaction, adjustment of pH of the liquor to a suitable range by adding neutralizer is most preferable. As for sucn neutralizer, $Ca(OH)_2$, NaOH, KOH, $Na_2CO_3$ or $CaCO_3$ can be used. As for the liquefaction bacteria, stirring and operation temperature, those which were used for the conventional anaerobic digestion method can also be employed effectively. For example, for liquefaction bacterium, Clostridium, Bacillus, Escherichia, Staphylococcus can be used. In general, these bacteria are used mostly as mixed group of bacteria rather than a single group. The gas generated at the liquefaction tank which is mostly carbon dioxide will get its $H_2S$ eliminated by a desulfurizer 8 before it is stored in gas reserve tank 9. The ingredients of the gas generated at the liquefaction tank vary widely depending on the variety of feedstock and treatment conditions, but generally their main ingredients are $CO_2$ 70–90% and $H_2$ 1–5%, with some small amounts of $N_2$ and $H_2S$. These gases are used either for dilution of high calorie and methane-rich gas that will be generated at the time of gasification at the subsequent step, or as a circulation gas for stirring aeration within the liquefaction tank 7.

Next, liquor 6 after liquefaction treatment will be charged into gasification tank 10, and by the activities of the gasification bacteria the organic acid will be converted into methane and carbon dioxide. In order to carry out this gasification efficiently, it is necessary to keep the temperature thermostatically within the range of normal to 75° C. and to adjust pH at 7–8, while keeping it fully stirred under an anaerobic atmosphere. Heating and stirring can be satisfactorily attained by the same methods as employed at the aforementioned liquefaction step. Adjustment of pH will be made by adding hydrochloric acid, sulfuric acid or organic acid. As for gasification bacteria, such conventionally used gasification bacteria as Methanosarcina, Methanococcus or Methanobacterium can be flully employed. The main ingredients of the gas generated are $CH_4$ 60–90% and $CO_2$ 10–40% with small amounts of $H_2S$, $N_2$ and $H_2$. Similar to the gas generated at the liquefaction step, the generated gas at this gasification step will be channelled through desulfurizer 12 and will be stored in gas reserve tank 13. The stored gas will be, as same as the case of conventional digestive process, will be used as a source of heating and as a power source for stirring.

The liquor that went through gasification treatment will be charged into solid liquor separator 14, and will be separated into separated water and digested sludge. The separation of solids and liquor at this step can easily be attained by such conventional methods as sedimentation separation or filtration. Digested sludge 15 generated from this step can be disposed as fertilizer after dehydrated and dried. Further, the separated water, being high in BOD concentration, will be put into aerobic treatment tank 16 and will be treated aerobically. As for this treatment, any of such publicly known aerobic treatment methods as activated sludge treatment, trickling filter treatment, catalytic oxidation treatment or rotary disk method can be applied. The separated water after aerobic treatment will be charged into solid liquor separator 18, and separated to treated water and excess sludge aerobically treated sludge 17 by a customary method.

Decomposed residue obtained from the first solid liquid separator 5 will be mixed with a part of treated water 19 and will be charged into solid liquor separator 20, where it will be separated to washed residue 21 and wash waste water 22. The wash waste water 22 is to be charged into the decomposition tank as mentioned earlier, and will be used for making a slurry of the feedstock, organic waste. Washed residue will be disposed out of the system as is or after dried, but it could also be re-used as a source of cellulose.

EXAMPLE 1

10 kg (dried weight 5 kg) of city garbage which was pulverized into particle sizes of 10–25 mm was charged in to a stainless steel heating tank of 100 liter, and was stirred after adding thereto 20 kg of wash water discharged from washing of decomposed residue cake by the digested separate water treated by activated sludge, as will be referred to later, and 80 gr of calcium hydroxide (95% purity), whereby a slurry of 9% solids concentration (organic concentration 7%) was prepared. The pH of this slurry was 9.8. This slurry was heated to 60° C. for 3 hours while being stirred at 200 rpm. Next, the slurry was processed through a filter press and 20.2 kg of extract water and 10 kg of cake (water content 65%) were obtained. Adding to the cake 6.7 liter of separate water treated with activated sludge, as subsequently mentioned, and 6.7 liter of wash water was obtained after stirring and squeezing by a filter press. Next, after repeating the same operation once again 6 liter in total of wash water was obtained. As a wash cake, 9 kg (water content 0.55 kg) was recuperated. Of the total solids of this cake, 90% was waste paper, and it contained as other ingredients plastics and sand, but it was not emitting any particular offensive odor even after it was left at room temperature for 3 days.

The extracted liquor obtained from decomposition treatment was charged in to a cylindrical stainless steel container having effective volume of 1.34 liter at the rate of 0.67 liter/day, and a continuous liquefaction treatment was carried out under the conditions of 200 rpm, 60° C., pH 5.8 and residential time 2 days. As an alkaline agent for adjusting pH, a slurry of 20% $Ca(OH)_2$ was used. The gas generated from the liquefaction tank contained $CO_2$ 90% (v/v), $H_2$ 7%, $H_2S$ 0.02% (v/v), and its generating rate was 4.9 liter/day. As seed bacteria for liquefaction, a liquefied slurry obtained through liquefaction treatment effected at least for over 2 weeks under the aforementioned conditions was used.

Next, the liquor treated by above liquefaction treatment was sent into a gasification tank having an effective volume of 4 liter, and gasification treatment was performed. Similar to the liquefaction tank, the gasification tank was also equipped with a stirrer, a jacket and an automatic pH adjuster. The conditions for gasification were residential time 6 days, 60° C., pH 7.5–7.9 and 200 rpm. Gas generation from the gasification tank averaged at 10 liter/day, and the gas contained $CH_4$ 70% (v/v), $CO_2$ 24%, $H_2$ 2% and $H_2S$ 0.02%. Next, the liquor after gasification treatment was carried in to a sedimentation separation tank having an effective volume continuously at the rate of 0.67 liter/day and held there for 12 hours, whereby 0.2 liter/day of gasification treatment sludge and 0.47 liter/day of separated water were obtained. Next, after adding 4 volume water to the separated water and carrying out an activated sludge treatment, 0.09 liter/day of excess activated sludge and 226 liter of treated water were obtained upon separating solids and liquor. Furthermore, as mentioned afore, a part of this treated water was used as wash water of the cake obtained from the decomposition treatment step.

EXAMPLE 2

The condensed garbage separate (hereafter condensed garbage waste), which was obtained by assorting city garbage, was crushed into particles of 10–25 mm by a pulverizer. The dry weight of this condensed garbage waste was 4.3 kg and its garbage containing rate on a dry base was 55%. 10 kg of the above pulverized condensed garbage waste was mixed with 25 kg of water and 35 kg of condensed garbage waste slurry was obtained. The solid concentration of this slurry was 12.3% (W/W) and its organic concentration was 9.0%.

First, 10 kg of the above condensed garbage waste slurry was charged into a 20 liter stainless steel beaker and its pH was adjusted to 9.5 by adding 39 gr of slaked lime (calcium hydroxide). It was kept heated at 60° C. for 3 hours while it was kept stirred at 100 rpm, and 10 kg of alkali decomposed slurry was obtained.

By processing 5 kg of the above alkali decomposed slurry through a filter press, 3.25 kg of filtrate and 1.75 kg of cake were obtained. The organic concentration of the filtrate was 4%. Of the above filtrate, 456 gr was taken out and charged into a 2 liter cylindrical fermentation tank (inner diameter 160 mm, height 120 mm). Next 1,160 gr of the anaerobically treated slurry of the condensed garbage waste slurry was added thereto as seed bacteria containing liquefaction and gasification bacteria. Then it was subjected to an anaerobic digestion at 60° C. while keeping its pH automatically at 7.0.

As for the seed bacteria which were used for the above digestion were prepared by adding water at the ratio of 1:2.5 weight/weight to the condensed garbage waste from the batch identical to the aforementioned one and by pulverizing it for 3 minutes by a home use mixer and by subjecting the slurry thereby obtained to a digestion treatment anaerobically for 25 days at 60° C. and 7.0 pH (run No. 2-a).

On the other hand, 700 gr was taken from the remaining alkali decomposed slurry and was charged into a 2 liter fermentation tank in a similar manner as the above together with 1,160 gr of seed bacteria which was taken from the batch identical to that was used in the above Example 1-a was subjected to an anaerobic digestion at 60° C. and 7.0 pH (run No. 2-b).

Next 10 kg of the above condensed garbage waste slurry was put into a 20 liter stainless steel beaker and its pH was adjusted to 3.5 by adding 70 gr of 35% hydrochloric acid. Thereafter, the slurry thus prepared was heated at 60° C. for 3 hours while being stirred at 100 rpm, and 10 kg of acid decomposed slurry was obtained. Of the above acid decomposed slurry, 5 kg was taken out and was processed through a filter press and 3.13 kg of filtrate and 1.78 kg of cake were obtained. The organic concentration within the filtrate was 4.1%. Then, 438 gr was taken out from the above filtrate and was charged into a 2 liter cylindrical fermentation tank (inner diameter 160 mm, height 120 mm). Next, as seed bacteria containing liquefaction and gasification bacteria, 1,160 gr of the digested slurry from the batch identical to run No. 2-a was charged in and an anaerobic digestion was performed at 60° C. while automatically adjusting its pH at 7.0 (run No. 2-c).

Besides the above, 700 gr was taken out from the remaining acid decomposed slurry, and was subjected to an anaerobic digestion together with 1,160 gr of seed bacteria from the same batch as used for the above run No. 2-a within a 2 liter fermentation tank at 60° C. and 7.0 pH in a similar manner as the above (run No. 2-d).

Next, 10 kg of the above condensed garbage waste slurry was charged into a 20 liter stainless steel beaker, and it was subjected to a heat treatment for 3 hours after adding 70 gr of water and while stirring at 100 rpm at 60° C., whereby 10 kg of heat treated slurry was obtained. Of the above heat treated slurry, 5 kg was taken out and was processed through a filter press, whereby 3.0 kg of filtrate and 2.0 kg of cake were obtained. The organic concentration within the filtrate was 1.6%. Of the above filtrate, 420 gr was taken out and was charged into a 2 liter cylindrical fermentation tank (inner diameter 160 mm, height 120 mm). Next, 1,160 gr of seed bacteria from the same batch as used for the above run No. 2-a was added and was subjected to an anaerobic digestion at 60° C. and 7.0 pH (run No. 2-e).

On the other hand, of the remaining heat treated slurry, 700 gr was taken out, and, together with 1,160 gr of the seed bacteria from the identical batch as was used for run No. 2-a, it was subjected to an anaerobic digestion within a 2 liter fermentation tank at 60° C. and 7.0 pH, in a similar manner as the above (run No. 2-f).

Next, 700 gr of the aforementioned condensed garbage waste slurry was taken out, and, together with 1,160 gr of the seed bacteria from the identical batch as was used for run No. 2-a, it was subjected to an anaerobic digestion within a 2 liter fermentation tank at 60° C. and 7.0 pH in a similar manner as above (run No. 2-g).

Of the aforementioned run No. 2-a through No. 2-g, those which correspond to the present invention are run No. 2-a and run No. 2-c, and the rest are comparative examples. The relations between the number of days required for digestion and the recovered volume of methane are shown in FIG. 2, and the economic comparison of the recovered volume of methane, power consumption and the volume of fermentation tank is shown in the table 1 attached.

contained in organic waste with a high digestion rate and low power consumption, at a high speed and under a condition where any possible trouble could be reduced almost to nil, and at the same time it facilitates an easy disposal of discharged residue and reduction of water consumption as well.

What is claimed is:

1. An anaerobic digestion process comprising the following steps:
   (1) Heating and stirring a mixture of crushed organic waste and the waste water obtained in step (9) at a temperature of 55°–75° C., while maintaining the pH of said mixture at 2.5–4.0 for making a slurry from said mixture,
   (2) Obtaining a separated liquid portion and a residue from the slurry recovered from the first step by solid/liquid separation,
   (3) Anaerobically digesting the separated liquid portion recovered from the second step under neutral to slightly alkaline conditions by introducing liquefaction and gasification bacteria to said liquid portion,
   (4) Obtaining separated water by removing digestive sludge from the slurry obtained from the third step by solid/liquid separation,
   (5) Aerobically treating the separated water obtained from step (4),
   (6) Obtaining an effluent by solid/liquid separation from the liquid aerobically treated in step (5),
   (7) Mixing together a part of the separated water obtained from step (6) with the residue obtained from the step (2),
   (8) Obtaining washed residue and waste wash water from the mixture at the seventh step by solid/liquid separation, and
   (9) Supplying said waste wash water obtained in step Table 1

|  | run No. 2- | Methane Recovered (N-CH$_4$/kg Condensed Garbage Waste) | Stirring Power Required (W, 2 l Fermenter Tank) | Number of Days for Fermentation (d) | Energy Consumed for Stirring (kwh) | Charged Volume (l) | Fermentation Tank Volume for 1 kg of Waste (l · d) |
|---|---|---|---|---|---|---|---|
| Present Invention | a | 17.8 | 14 | 5.0 | 1.7 | 1.62 | 41 |
|  | c | 17.1 | 14 | 5.0 | 1.7 | 1.60 | 40 |
| Comparative Examples | b | 21.8 | 32 | 12.0 | 9.2 | 1.86 | 112 |
|  | d | 21.4 | 28 | 12.0 | 8.1 | 1.86 | 112 |
|  | e | 7.1 | 18 | 4.5 | 1.9 | 1.58 | 36 |
|  | f | 17.4 | 45 | 15.0 | 16.2 | 1.86 | 140 |
|  | g | 16.7 | 62 | 22.0 | 32.7 | 1.86 | 205 |
|  | h* |  | 8 |  |  |  |  |

*1.9 liter of water was charged into a 2 liter fermentation tank and the required stirring power was measured.

As it is clearly understood from FIG. 2 and the table 1, an acid decomposition treatment or alkali decomposition treatment enables to shorten the number of days required for fermentation considerably, as compared with the case of untreated or a heat treatment alone. Furthermore, if the filtrate obtained by solid/liquid separation after acid decomposition or alkali decomposition is used, the time required for fermentation could be markedly reduced and the saving in the stirring power is remarkable, whereas the recovery of methane would be reduced by about 20% as compared with the direct digestion of the decomposed slurry. Also it will be known that the dimension of the fermentation tank could be minimized to a great extent.

As detailed in the above, the present invention enables an anaerobic digestion of digestible ingredients (8) to step (1).

2. The anaerobic digestion process of claim 1, wherein said step (3) where anaerobic digestion is performed includes a gasification treatment for generating methane and carbon dioxide by the activity of gasification bacteria at from neutral to slightly alkaline conditions, after a liquefaction treatment is performed by the activity of liquefaction bacteria under from slightly acidic to neutral conditions.

3. The anaerobic digestion process of claim 2, wherein said liquefaction bacterium used in step (3) is at least one member selected from the group consisting of Clostridium, Bacillus Escherichia and Staphylococcus.

4. The anaerobic digestion process of claim 2, wherein said gasification bacterium is at least one member selected from the group consisting of Mechanosarcina Methanococcus and Methanobacterium.

5. An anaerobic digestion process of claim 1, wherein an acid is used to maintain the pH of said mixture at 2.5-4.0 in step (1), said acid is at least one member selected from the group consisting of mineral acids and organic acids.

6. The anaerobic digestion process of claim 5, wherein the acid used is a mineral acid, and said mineral acid is at least one member selected from the group consisting of hydrochloric acid and sulfuric acid.

7. The anaerobic digestion process of claim 5, wherein the acid used is an organic acid, and said organic acid is at least one member selected from the group consisting of acetic acid and citric acid.

8. The anaerobic digestion process of claim 1, wherein said liquefaction bacterium used in step (3) is at least one member selected from the group consisting of Clostridium, Bacillus Escherichia and Staphylococcus.

9. The anaerobic digestion process of claim 1, wherein said gasification bacterium used in step (3) is at least one member selected from the group consisting of Methanosarcina, Mechanococcus Methanobacterium.

10. The anaerobic digestion process of claim 1, wherein the pH of said separated liquid portion in said gasification treatment is maintained from 7 to 8.

11. The anaerobic digestion process of claim 1, wherein step (3) is carried out at a temperature between room temperature and 75° C.

12. The anaerobic digestion process of claim 1, wherein the pH of the separated liquid portion in said liquefaction treatment is maintained from 4 to 7.

13. An anaerobic digestion process comprising the following steps:
  (1) Heating and stirring a mixture of crushed organic waste and the waste wash water obtained in step (9) at a temperature of 55°-75° C., while maintaining the pH of said mixture at 8.0-9.8 for making a slurry from said mixture,
  (2) Obtaining a separated liquid portion and a residue from the slurry recovered from the first step by solid/liquid separation,
  (3) Anaerobically digesting the separation liquid portion recovered from the second step under neutral to slightly alkaline conditions by introducing liquefaction and gasification bacteria to said liquid protion,
  (4) Obtaining separated water by removing digestive sludge from the slurry obtained from the third step by solid/liquid separation,
  (5) Aerobically treating the separated water obtained from step (4),
  (6) Obtaining an effluent by solid/liquid separation from the liquid aerobically treated in step (5),
  (7) Mixing together a part of the separated water obtained from step (6) with the residue obtained from the step (2),
  (8) Obtaining washed residue and waste wash water from the mixture at the seventh step by solid/liquid separation, and
  (9) Supplying said waste wash water obtained in step (8) to step (1).

14. The anaerobic digestion process of claim 13, wherein an alkali is used to maintain the pH of said mixture at 8.0-9.8 in step (1), is at least one member selected from the group consisting of calcium hydroxide, calcium oxide, and carbide residue from acetylene production.

15. The anaerobic digestion process of claim 13, wherein said step (3) where anaerobic digestion is performed includes a gasification treatment for generating methane and carbon dioxide by the activity of gasification bacteria at from neutral to slightly alkaline conditions, after a liquefaction treatment is performed by the activity of liquefaction bacteria under from slightly acidic to neutral conditions.

16. The anaerobic digestion process of claim 15, wherein said liquefaction bacterium used in step (3) is at least one member selected from the group consisting of Clostridium, Bacillus Escherichia and Staphylococcus.

17. The anaerobic digestion process of claim 15, wherein said gasification bacterium is at least one member selected from the group consisting of Mechanosarcina Methanococcus and Methanobacterium.

18. The anaerobic digestion process of claim 13, wherein said liquefaction bacterium used in step (3) is at least one member selected from the group consisting of Clostridium, Bacillus Escherichia and Staphylococcus.

19. The anaerobic digestion process of claim 13, wherein said gasification bacterium used in step (3) is at least one member selected from the group consisting of Methanosarcina, Mechanococcus Methanobacterium.

20. The anaerobic digestion process of claim 13, wherein the pH of said separated liquid portion in said gasification treatment is maintained from 7 to 8.

21. The anaerobic digestion process of claim 13, wherein step (3) is carried out at a temperature between room temperature and 75° C.

* * * * *